United States Patent [19]

Korth

[11] Patent Number: 5,696,114
[45] Date of Patent: Dec. 9, 1997

[54] TREATMENT AND PREVENTION OF ODEMA

[76] Inventor: Ruth Korth, Palestrinastrasse 9, D-8000 München 19, Germany

[21] Appl. No.: 246,476

[22] Filed: May 19, 1994

Related U.S. Application Data

[63] Continuation of Ser. No. 968,878, Oct. 30, 1992, abandoned.

[30] Foreign Application Priority Data

Nov. 4, 1991 [EP] European Pat. Off. ............ 91118744.1

[51] Int. Cl.$^6$ .................. A61K 31/55; A61K 31/595; A61K 31/56; A61K 31/44
[52] U.S. Cl. .................. 514/219; 514/168; 514/171; 514/222; 514/282
[58] Field of Search .................. 514/168, 171, 514/222, 282, 219

[56] References Cited

U.S. PATENT DOCUMENTS

| | | | |
|---|---|---|---|
| 4,183,912 | 1/1980 | Rosenthale | 424/45 |
| 4,595,693 | 6/1986 | Biftu | 514/461 |
| 4,621,083 | 11/1986 | Casals | 514/220 |
| 4,900,729 | 2/1990 | Stransky | 514/220 |
| 5,147,864 | 9/1992 | Wissner | 514/82 |
| 5,202,313 | 4/1993 | Bombardelli et al. | 514/100 |
| 5,334,592 | 8/1994 | Billah | 514/220 |

FOREIGN PATENT DOCUMENTS

| | | |
|---|---|---|
| A-869 136 | 1/1979 | Belgium . |
| A-902 874 | 11/1985 | Belgium . |
| 0-151687 | 8/1985 | European Pat. Off. . |
| A-2830782 | 1/1980 | Germany . |
| A-87/05890 | 9/1985 | Spain . |
| WO-90/13299 | 11/1990 | WIPO . |

OTHER PUBLICATIONS

Kornecki and Ehrlich, Science 240 (1988) 1792–1794 Neuroregulatory and Neurophathological Actions of the Ether–Phospholipid Platelet–Activating Factor.

Aronoux et al., A Rev. Respir Dis 137 (1988) 855–860 "Accumulation of Platelets and Eosinophils in Baboon Lung after PAF–Acether Challenge, Inhibition of Ketotifen".

Kroegel et al. J. Immunol. 142 (1989) 3518–3526, "Stimulation of Degranulation from human Eosinophils by Platelet–activating factor."

Snyder, Biological Membranes: Aberrations in Membrance Structure and Function (1988), 57–72, "Metabolism of Platelet Activating Factor and Related Ether Lipids: Enzymatic Pathways, Subcellular Sites, Regulation, and Membrane Processing."

Brasseur et al. Biochem. Biophys. Acta 1085 (1991) 91–105, "PAF–receptor III Conformational and Electronic Properties of PAF–like Agonists and Antagonists".

Kornecki et al. Adv. Exp. Med. Biol. 221 (1987) 477–488, "Interactions of the alkyl–ether–phospholipid, platelet activating factor (PAF) with platelets, neural cells, and the psychotropic drugs triazolobenzodiazepines".

Kornecki et al., Science 226 No. 4681 (1984) 1454–1456, "Platelet–activating factor–induced aggregation of human platelets specifically inhibited by triazolobenzodiazepines."

Tiberghien C et al. J. Lipid Mediat, vol. 3, No. 3 (1991) 249–266, A competitive receptor binding assay for platelet–activating factor (PAF): Quantification of PAF in rat brain.

Gulbenkian et al. Am. Rev. Respir. Dis. vol. 142 No. 3 (1990) 680–685 "Anaphylactic challenge causes eosinophil accumulation in bronchoalveolar lavage fluid of guinea pigs. Modulation by betamethasone, phenidone, indomethacin, WEB 2086, and novel antiallergy agent, SCH 37224".

Abrahan et a. J. Appl. Physiol. vol. 66, No. 5 (1989) 2351–2357 "A possible role for PAF in allergen–induced late responses: Modificaiton by a selective antagonist."

Korth and Benveniste Eur. J. Pharmacol. 142 No. 3 (1987) 331–341 "BN 52021 displaces [3H]paf–acether from, and inhibits its binding to intact human platelets."

Otamiri et al. Gut, vol. 29, No. 4 (1988) 489–494 "Phospholipase A2 inhibition prevents mucosal damage associated with small intestinal ischaemia in rats."

Etienne et al. Agents and Actions vol. 17 No. 3–4 (1985) 368–370 "In Vivo inhibition of plasma protein leakage and salmonella enteritids–induced mortality in the rat by a specific Paf–acether antagonist BN 52021."

Chan–Yeung et al. J. All. Clin. Immunol. 87 (1991) 667–673, "The release of platelet–activating factor into plasma during allergen–induced bronchoconstriction."

Yue et al. J. Pharm. and Exp. Ther. 254 (1990) 976–981, "Protective effect of BN 50739, a new platelet–activating factor antagonist, in endotoxin–treated rabbits."

Bousquet et al. New Engl. J. 323 (1990) 1033–1039, "Eosinophilic inflammation in asthma."

Fradin et al. Biochim. Biophys. Acta 963 (1988) 248–257, "Inhibition of eicosanoid and PAF formation by dexamethasone in rat inflammatory polymorphonuclear neutrophils may implicate lipocortin 's'."

*Primary Examiner*—Theodore J. Criares
*Attorney, Agent, or Firm*—Nikaido, Marmelstein, Murray & Oram LLP

[57] ABSTRACT

The invention refers to the treatment and prevention of eosinophil-mediated diseases with paf antagonists and a procedure for determining their efficacy. According to the invention for treating and prevention a disease mediated by eosinophils a combination with an effective amount of at least one paf antagonist is administered to a subject requiring said treatment of allergy and inflammation, wherein the paf antagonist is a hydrophilic or non-hydrophilic triazolothieno-diazepine or a homologue thereof, a ginkgolide, a ginkgolide mixture or a synthetic ginkgolide derivate, or an analogue of the paf or a mixture with/of these compounds.

1 Claim, 5 Drawing Sheets

TREATMENT AND PREVENTION OF ODEMA

This application is a continuation of application Ser. No. 07/968,878 filed Oct. 30, 1992 now abandoned.

FIELD OF THE INVENTION

The invention refers to the treatment and prevention of eosinophil-mediated diseases and oedemas in combination with paf antagonists and a procedure for determining their efficacy.

SUMMARY OF THE INVENTION

Paf, (1-O-alkyl-2-acetyl-sn-glycero-3-phosphocholine) was originally described as a mediator of the acute phase of allergic diseases, because it is released by IgE-sensitized basophils (Benveniste et al., 1972, J. Exp. Med. 136, 1356). Paf activates various blood cells via specific paf receptors, resulting beside other effects, in a cytosolic $Ca^{2+}$ rise. Specific paf receptor antagonists such as ginkgolides, hetrazepines such as WEB 2086 and paf analogues inhibit paf-mediated cell activation (Korth et al., 1988, Eur. J. Pharm. 152, 101; Korth et al., Br. J. Pharmacol., 1989, 98, 653; Korth, Eur. patent applications 0 312 913 and 91108763.3; Hwang et al. 1985, Biochem. Biophys. Res. Comm. 128, 972; Braquet, UK patent GB 2162062A; Takeda Chem. Industries, U.S. Pat. Nos. 4,582,824; Casals-Stenzel et al. U.S. Pat. No. 4,621,083).

Paf is a potent chemotactic factor for human eosinophils, regulates IgE binding to normal density eosinophils, superoxide formation and eosinophil degranulation as well as their adherence to endothelial cells (for review Hwang, 1990, J. Lipid Med. 2, 123).

Surprisingly enough, it has now been discovered that the presence of low (5 and 10 mM) concentrations of unlabeled paf decreased the inhibitory effect of the paf antagonist WEB 2086 on [$^3$H]paf binding to eosinophils in a significant and specific manner. According to the present invention, eosinophil-mediated diseases-for example allergic and/or inflammatory diseases should be successfully treated by combination of specific paf receptor antagonists with drugs lowering the level of paf in blood, plasma or tissue for example by inhibition of pal synthesis and/or addition of non-specific paf antagonists. This conclusion is based on our finding that paf receptors on intact human blood eosinophils are downregulated in the presence of submaximal level of paf with inefficiency of specific paf receptor antagonists shown here with WEB 2086. According to our invention, drugs lowering the level of paf in the blood, plasma and/or tissue can be for example classical antiallergic and antiinflammatory drugs such as glucocorticosteroids which decrease paf synthesis via interaction with phospholipase $A_2$ end/or drugs which decrease a histamine-mediated paf synthesis. Other antagonists of paf synthesis have been developed such as antiflammins (Tetta et al. J. Pharmacol. Exp. Therapeutics 257, p 616, 1990) which might also be more effective in combination with specific paf receptor antagonists. In addition, side effects of classical antiallergic and/or antiinflammatory drugs for example oedema formation after addition of glucocorticosteroids or central nervous symptoms after addition of drugs against histamine could be reduced by combination with paf receptor antagonists. In this context, paf receptor antagonists could reduce side effects of antiallergic and/or antiinflammatory drugs either causatively by antagonizing for example steroid-mediated oedema formation by protection of the endothelial barrier (R. Korth, European Patent No. 0312913) or indirectly by reducing the dose of the classical drugs which induce side effects. Two other important groups of antiallergic and/or antiinflammatory drugs are those modulating either the cellular level of cyclic adenosine monophosphate (cAMP) directly (for example theophylline or prostacyclin) or via heterologous receptor interaction for example drugs interacting with adrenergic β-receptors to modulate various other receptors to avoid the development of tolerance. Finally, non-specific paf antagonists should be tested and repaired such as paf degrading enzymes and/or paf antagonizing lipids or proteins including antibodies.

In this connection, when platelets were aggregated in response to high concentrations of paf (100 nM), they released a part of their paf degrading acetylhydrolase. Finally it has been discovered that a long lasting increase of cyclic adenosine monophosphate (cAMP) expressed paf receptors on monocyte/macrophage cell lines and this was partly prevented by the paf receptor antagonist WEB 2086.

Although antagonists' of paf synthesis are ,not yet available, it is known that the synthesis is mediated by the activity of the phospholipase $A_2$ via the production of the paf precursor lyso paf. The activity of the phospholipase $A_2$ increases in parallel with cAMP (Pfeilschifter et al. Eur. J. Biochem., 1989, 181, 237; for review E. Ninio, New Horizons in Platelet Activating Factor Research Ed. by C. M. Winslow and M. L. Lee 1987, John Wiley & Sons Ltd.). In addition, we have discovered here that serum albumin competes with paf receptors for paf binding as a natural non-specific paf antagonist. As serum albumin is reduced in hepathic and nephrotic oedema paf antagonists seem to suitable in these cases. Fish liver oils (N-3 polyunsaturated fatty acids) has been shown to decrease the paf synthesis in human cells (Sperling et al. 1987, 139, 4186) and is commercial available now for the treatment and prevention of allergic, inflammatory and hyperlipidemic as well as cardiovascular diseases. Prostacyclin with analogues and garlic oils are also commercial available for the prevention and treatment of allergy, inflammations and hyperlipidemic as well as cardiovascular diseases via modulation of the cAMP level.

As we have found, that the presence of submaximal concentrations of paf inhibited the binding sites of paf receptor antagonists on esoinophils, it is suitable to combine paf receptor antagonists with a compound which decrease the blood level of paf. In this connection an additional compound is suitable to inhibit paf synthesis for treating and preventing eosinophil-mediated diseases such as inflammations, allergies, including asthma, oedema (including hepatic and nephrotic oedemas) and anaphylactic shock. These treatments should prevent that submaximal levels of paf induce eosinophil emigration into the tissue with eosinophil-mediated tissue damage and reduce the responsiveness of eosinophils to paf receptor antagonists. On the long term however, it is suitable to develop compounds according to the invention which inhibit paf receptors and prevent synthesis of pal at the same time. It is also suitable to increase paf degradation for example by an increase of acetylhydrolase release from platelets.

The substance that are shown to inhibit the paf binding sites in this connection can be a triazolo-thieno-diazepine or a homologous compound. In addition ginkgolides and paf analogues, such as CV 3988, have proven suitable. Triazolothieno-diazepines are described in Br. J. Pharmacol. 1987, 90, 139, ginkgolides in "Blood and Vessel" 1985, 16, 558. Of the triazolothieno-diazepine compounds WEB 2086 and WEB 2098 are especially suitable. Of the ginkgolides BN 52020, BN 52021 and a mixture of BN 52020, BN 52021 and BN 52022, which is referred to as BN 52063, achieve the best results. The synthetic compound BN 50739 can also be used.

The chemical term of CV 3988 is rac-3-(N-n-octadecyl carbamoyl oxy)-2-methoxypropyl 2-tiazolioethyl phosphate; the term of WEB 2086 is 3-(4-(2-chlorophenyl)-9-methyl-6H-thieno(3,2-f) (1,2,4)triazolo-(4,3-a)-(1,4)diazepine-2yl)-1-(4-morpholinyl)-1-propanone; the term of WEB 2098 is (3--(4-(2-chlorophenyl)-9-cyclopropyl-6H-thieno(3,2-f)-(1,2,4)triazolo-(4,3-a) (1,4)diazepine-2yl)-1-(4-morpholinyl)-1-propanone; the term of BN 52020 is 9H-1, 7a-Epoxymethano)-1H, 6aH-cyclopenta(c)furo(2,3-b)furo(3',2':3,4) cyclopenta (1,2-d)furan-5,9,12 (4H)-trione, 3-tert-butylhexahydro-4,7b-dihydroxy-8-methyl; the term of BN 52021 is 9H-1, 7a-Epoxymethano)-1H,6aH-cyclopenta(c)furo(2,3-b)furo-(3',2':3,4) cyclopenta(1,2-d)furan-5,9,12(4H)-trione, 3 tert-butylhexahydro-4, 4b-11-trihydroxy-8-methyl; and the term of BN 52022 is 9H-1, 7a-(Epoxymethano)-1H,6aH-cyclo-penta(c)furo(3',2':3,4) cyclopenta(1,2-d) furan-5,9,12 (4H)-trione, 3 tert-butyl hexahydro-2,4,7b,11-tetrahydroxy-8-methyl. The chemical term of BN 50739 is tetrahydro-4,7,8,10 methyl (chloro-2 phenyl)6 (dimethoxy-3,4-phenyl)thio)methylthiocarbonyl-9 pyrido (4',3'-4,5)thieno(3,2-f)triazolo-1,2,4(4,3-a)diazepine-1,4).

The paf antagonist can be administered topically, orally, parenterally or by inhalation. The compounds are administered as active ingredients in conventional pharmaceutical preparations, e.g. in compositions comprising an inert pharmaceutical vehicle and an effective dose of the active substance, such as tablets, coated tablets, capsules, lozenges, powders, solutions, suspensions, aerosols for inhalation, ointments, emulsions, syrups, suppositories, etc. The effective dose range of the compounds according to the invention includes at least 10 to 500, preferably between 0, 1 and 50 mg per dose for intravenous or intramuscular application.

In other words, according to the invention, substances should be tested and developed whose eosinophil binding sites are either not downregulated by paf itself and/or prevent the synthesis of paf and/or increase the paf degrading activity.

In order to conduct a quick and simple test on the efficacy with regard to their antagonistic activity vis-à-vis paf receptors on eosinophils, i.e. to use a screening procedure, for example, to find effective antagonists to paf receptors on eosinophils which can then be taken into consideration for treating the diseases mentioned, then according to the Invention, the best method is to proceed as follows.

a) Paf-like compounds and paf degradation are measured in given biological tissues.

b) eosinophils are washed, c) a given quantity of eosinophils is mixed with a given quantity of labeled paf and of the paf antagonist to be determined in the presence and absence of low and concentrations of paf, d) a given quantity of eosinophils is mixed with a given quantity of labeled paf in the presence and absence of low and concentrations of paf, e) the cells are separated from the mixtures d) and e) in each case, f) the quantity of marked paf bound to eosinophils is measured in each case, and g) the efficacy of the paf antagonist is determined from the relationship between on the one hand the quantity of marked paf which is bound to eosinophils in the presence of low and said concentrations of paf according c) in the presence of the antagonist, and on the other hand the quantity of labeled paf which is bound to the eosinophils according to d) in the absence of the antagonist, related to the same number of eosinophils.

In accordance with step a) paf-like compounds and the activity and release of acetylhydrolase is measured in the biological tissue preferably as described in the European patent application 91108763.3.

Preferably, eosinophils are used as cells for the procedure of the invention for determining the efficacy of paf antagonists.

In case eosinophils are used, they are washed according to the invention preferably under sterile conditions to avoid cell activation with an arteficial downregulation of pal receptors. Thereafter the purified cells are preferably dispersed in an isotonic buffer containing delipidated serum albumin, but no calcium ions. In case eosinophils are used they are concentrated several times before they are used in steps b) and c) in the procedure according to claim 5 in the presence of calcium and magnesium ions. Besides eosinophils also eosinophil cultures and/or cell lines can be used to test and use similar effects on the genetic level.

As labeled ligands tritium-labeled paf, labeled LA-paf, labeled antagonists such as labeled hetrazepines, paf analogues or ginkgolides can be used, for instance. It is also possible to use labeled and unlabeled antibodies against the paf as well as coloured or fluorescence labeled compounds.

The mixing according to the steps b) and c) of claim 5 is done preferably at a temperature of 20° C. because at 4° C. the homologous downregulation cannot be detected. After mixing, the cells are incubated preferably 30 min. before they are separated according to step d) of the procedure of the present invention. The separation of the cells according to step d) can be performed by filtration or centrifugation.

After this, the quantity of labeled paf which is (specifically) bound to the cells is determined. If radioactively labeled paf is used, only the radioactivity bound to eosinophils is measured. The radioactivity bound in the filter where there are no cells is subtracted from these values.

By drawing calibration graphs, which are obtained with varying quantities the antagonist in accordance with step b), it is thus possible to obtain the efficacy of the antagonist at a 50% inhibitory value, i.e. as that quantity of the antagonist which, in relation to a given quantity of cells, leads to a 50% inhibition of the reversible paf binding.

The procedure of the present invention in which downregulation of eosinophil receptors by submaximal (preferably 5 and 10 nM) paf concentrations is used has been tested successfully particularly with WEB 2086 as triazolothieno-diazepine. Paf antagonists can be preferably tested in screening procedure according to the present invention using freshly prepared eosinophils, eosinophils in culture or cell lines.

Monoclonal or polyclonal antibodies against paf receptors on eosinophils can be tested and formed for simple and quick diagnostic clinical tests (for example microscopical analysis) preferably in a coloured or fluorescence form as the volume of blood which is necessary to prepare blood eosinophils is very high. Finally paf receptors are stable for five days in special testing containers and thus the receptor status of blood eosinophils can be investigated in central institutes when blood is taken into special testing containers which are commercial available and which should be modified for smaller blood volumes as proposed in German utility model application G87 16 004.8.

Since the specific binding of paf or paf-like compounds is in close correlation with the cellular calcium stream, the procedure of the present invention can also be used for measuring the effect of paf or paf like compounds on eosinophils by comparing their effect on the cellular calcium stream with calibration graphs of synthetic paf.

The following three examples serve to explain the invention more clearly:

EXAMPLE 1

Homologous Downregulation of Binding Sites for paf Receptor Antagonists on Human Eosinophils In the Presence of Submaximal paf Concentrations 1.1. Methods Tyrode's buffer and ACD were composed and compounds were dissolved as described (Korth et al., 1989, 98, 653–661). Origin of the reagents used: fatty acid-free bovine serum albumin (BSA, fraction V, sigma Chem., St. Louis, Mo., U.S.A.); [$^3$H]paf (1 -O-[$^3$H]-octadecyl-2-acetyl-sn-glycero-3-phosphocholine, 80 Ci/mmol) and ACS scintillation fluid (Amersham, Amersham, U.K.), unlabeled synthetic paf (1-octadecyl-2-acetyl-sn-glycero-3-phosphocholine); its enantiomer; lyso paf (1-octadecyl-sn-glycero-3-phosphocholine) and 2-lysophosphocholine (LPC) (Bachem, Bubendorf, Switzerland); WEB 2086 was solubilized in water with 0.1N HCl ultrasonically every day. Whatman GF/C filters (Ferriére, France); Millipore vacuum system from Molsheim (F.R.G); Fura-2-AM (Calbiochem, F.R.G.); fluorescence spectrophotometer (RF-500) from Shimadzu (Kyoto, Japan)

1.2. Preparation of eosinophils:

Eosinophils were prepared as described (Vadas et al., 1979, J. Immunol. 122, 1228) with slight modifications. Blood (400 ml) was mixed with 10% (v/v) dextran. The supernatant was carefully deposited on a metrizoate/ficoll suspension (d=1.148) after sedimentation of red blood cells and centrifuged (400×g: 40 min). Erythrocyte lysis was performed by adding 3 v. of distilled water for 40 sec, followed by 1 v. NaCl (3.5%, w/v). Cells were suspended in 500 μl pH 7.4 Tyrode's buffer, centrifuged (1900 rpm×10 min) and resuspended (5×10$^6$ cells/ml) in Tyrode's (0.25% BSA) without Ca$^{2+}$. The eosinophils fraction at 1×10$^6$ cells/ml contained 96±5% eosinophils, 3±3% neutrophils, 1±2% monocuclear cells and no free platelets (mean±s.d., n=3) (Beauvais et al., 1990, J. Immunol. 144, 3881).

1.3. [$^3$H]paf binding studies;

[$^3$H]paf Binding to eosinophils (2.5×10$^5$/500 μl) was performed as described (Korth et al., 1986, Thrombos. Res. 41, 699). Eosinophils were added to Tyrode's (0.25% BSA, 1.3 mM CaCl$_2$, 1 mM MgCl$_2$) containing [$^3$H]paf (0.325–6.5 nM) in the absence or presence of unlabeled paf, lyso paf, enantio-paf or lyso-phosphatidylcholine (LPC) (5, 10, 50, 500 nM) and/or the specific pal receptor antagonist WEB 2086 (400 nM). Incubation was performed for 30 min at 20° C. or 20 hrs at 4° C. Cell-bound radioactivity on the filters after vacuum filtration from where blanks were subtracted was calculated as fmol [$^3$H]paf bound per 2.5×10$^5$ eosinophils. [$^3$H]paf metabolism of eosinophils was excluded in parallel experiments (not shown) as described (Korth et al., 1988, Eur. J. Pharmacol. 152, 101–110). Preliminary experiments indicated that eosinophil-bound [$^3$H]paf could not be displaced by WEB 2086 (not shown).

1.4. Cytosolic free calcium:

The concentration of cytosolic free calcium ([Ca$^{2+}$]i) was measured using the Ca$^{2+}$ indicator fura-2-acetoxymethyl ester (fura-2) as described (Grykiewicz et al., 1985, J. Biol. Chem. 260, 3440). Eosinophils (2×10$^7$/ml) in Tyrode's (0.25% BSA, no CaCl$_2$) were incubated for 30 min at 37° C. with 2.5 μM fura-2 and resuspended In Tyrode's (0.25% BSA) in the presence of 2 mM EGTA. Paf was added to eosinophils (5×10$^5$ per ml) at increasing concentrations (1–100 nM) under stirring, 3 min after addition of WEB 2086 (1 μM) or vehicle.

2. Results 2.1. Specific [$^3$H]paf binding to eosinophils:

In 3 experiments eosinophils bound [$^3$H]paf in a concentration-dependent manner after 20 hrs Incubation at 4° C. The specific [$^3$H]paf binding assessed either with unlabeled paf (500 nM, FIG. 1A) or the specific paf receptor antagonist WEB 2086 (400 nM, FIG. 1B) reached similar maximal plateau values (14.0±9.0 and 14.8±5.1 fmol per 2.5×10$^5$ cells) at concentrations higher than 3.25 nM added [$^3$H]paf. The binding affinity (K$_d$) was 5.5 nM with B$_{max}$ of 35.4 fmol per 2.5×10$^5$ cells, corresponding to 85×10$^3$ binding sites per eosinophil.

However, at 20° C. (30 min, n=6), we encountered 2 different cell populations. In 3 experiments specific [$^3$H]paf binding, verified with WEB 2086 (400 nM), reached plateau values (25.8±8.1 fmol) whereas in 3 other experiments no inhibitory effect of WEB 2086 was observed (4.3±3.3 fmol) indicating a lack of specific binding.

No additive inhibitory effects on [$^3$H]paf binding were found when both WEB 2086 (400 nM) and unlabeled paf (50 to 500 nM) were added together neither at 4° C. nor at 20° C. (Table 1). Lyso paf (Table 1), enantio paf and LPC (not shown) did not interfere with [$^3$H]paf binding.

2.2. Effect of paf on the inhibitory effect of WEB 2086:

The inefficiency of WEB 2086 in 3 of 6 experiments at 20° C. could be attributed to a downregulation of paf receptors. We thus investigated the effect of low concentrations of paf on WEB 2086 efficacy. Indeed, the presence of low concentrations of unlabeled paf (*5 and *10 nM, not 50 and 500 nM) decreased the Inhibitory effect of WEB 2086 on [$^3$H]paf binding in a significant manner (Table 1, *p<0.01, using the "Mann Whitney" test, n=8). These phenomena were specific as the paf metabolite lyso paf, the enantio-paf or LPC were unable to modulate the effect of WEB 2086.

Figure 2:
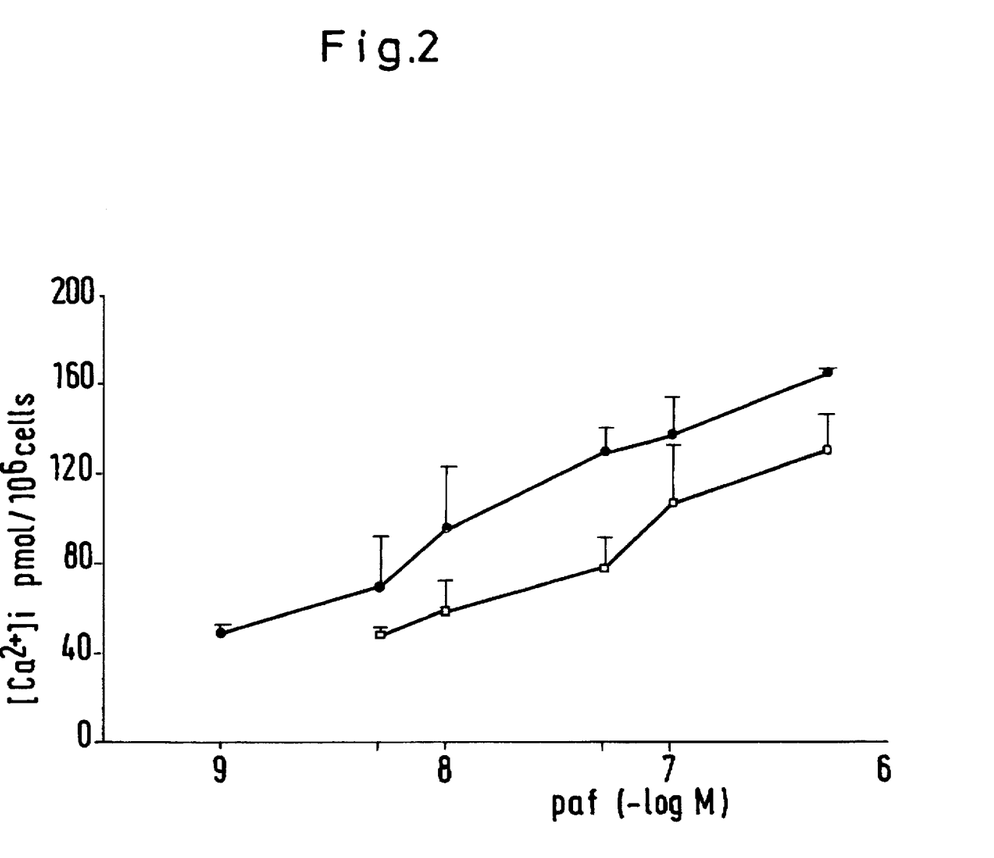
FIG. 2 is a plot of paf dose-response curve of the cytosolic Ca$^{2+}$ flux.

2.3. Cytosolic Ca$^{2+}$ flux of eosinophils in response to paf:

The function of specific paf binding sites on intact human eosinophils was explored by monitoring [Ca2+ ]i rise in response to paf. Addition of paf (1–100 nM) to fura-2-loaded eosinophils in a Ca$^{2+}$ free buffer in the presence of EGTA (2 mM) produced a concentration-dependent elevation of [Ca$^{2+}$]i (FIG. 2). WEB 2086 competitively inhibited the paf-mediated [Ca$^{2+}$]i rise as It shifted to the right the dose-response curve in a parallel manner.

Figure 1A:
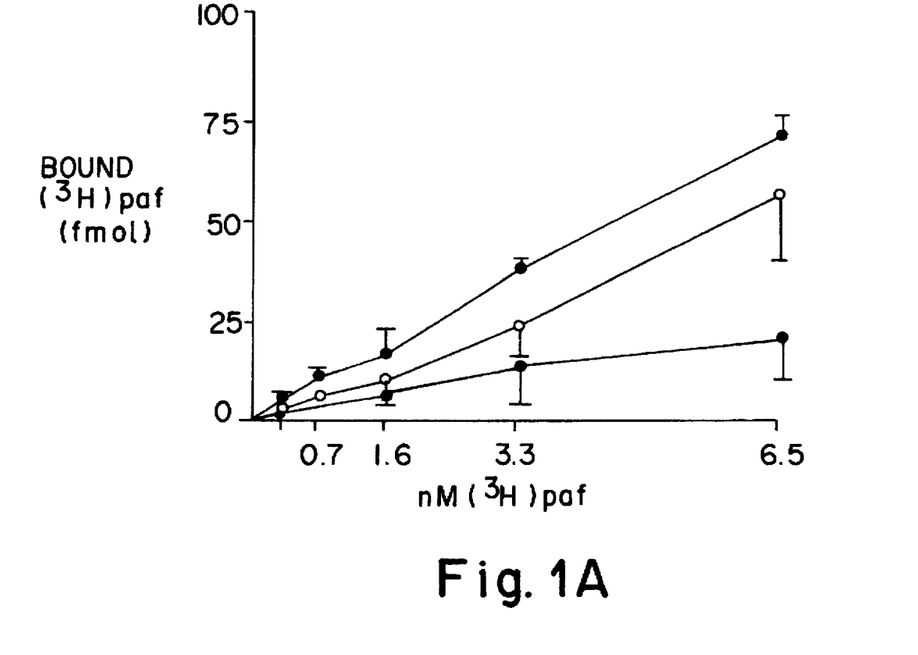
FIG. 1 is a plot of [$^3$H]paf binding to intact human eosinophils at 4° C.
Figure 1B:
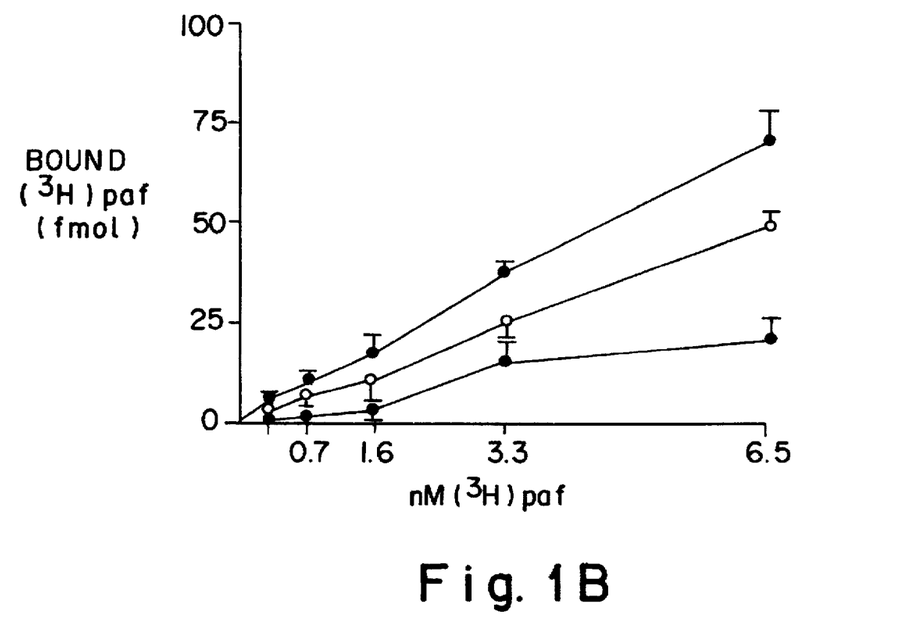

3. Legends and Table:

FIG. 1: [$^3$-H]paf binding to intact human eosinophils at 4° C. Eosinophils ($2.5 \times 10^5$ per 500 µl) were incubated in the presence of [$^3$H]paf concentrations as shown for 20 hrs at 4° C. before vacuum filtration. Non-specific binding was assessed with 500 nM unlabeled paf (A,○) or the specific paf receptor antagonist 400 nM WEB 2086 (B,□). The specific binding (■) was calculated as total (●) minus non-specific binding. Values are means±1 s.d. of 6 experiments. FIG. 1 shows an inhibition of paf receptors on human eosinophils by WEB 2086.

FIG. 2: Paf dose-response curve of the cytosolic $Ca^{2+}$ flux. Eosinophils ($10^5$ per ml) were incubated for 3 min at 37° C. under stirring with WEB 2086 (□) or vehicle (●) before paf was added at the concentrations as shown in a buffer devoid of $CaCl_2$, containing 2 mM EGTA. Values are means±1 s.d. of 3 experiments. FIG. 2 shows that the inhibitory effect of WEB 2086 on eosinophil paf receptors is functional relevant.

TABLE 1

Unlabeled paf decreased the specific [$^3$H]loaf binding in the presence of WEB 2086.

| Addition of paf and lyso paf (nM) | paf | WEB 2086 + paf (n = 8) | lyso paf (n = 3) | WEB 2086 + lyso paf (n = 3) |
|---|---|---|---|---|
| 0 | — | 15.1 ± 8.0[1] | — | — |
| 5 | 3.8 ± 5.0 (n = 4) | *7.1 ± 5.0 | 1.5 ± 1.7 | — |
| 10 | 4.3 ± 2.9 (n = 5) | *2.3 ± 2.9 | 1.2 ± 1.6 | 14.3 ± 6.9 |
| 50 | 7.2 ± 5.4 (n = 8) | 18.4 ± 11.8 | 4.4 ± 3.7 | 14.9 ± 7.5 |
| 500 | 12.5 ± 6.9 (n = 4) | — | — | — |

*p<0.01 as compared to WEB 2086 with paf vehicle
[1]in a "Mann Whitney" test, n = 8.

The specific [$^3$H]paf binding was assessed with WEB 2086 (400 nM, 20° C., 30 min) in the presence or absence of the indicated concentrations of unlabeled paf and lyso paf. The inhibitory effect of WEB 2086 (specific) [$^3$H]paf binding decreased significantly in the presence of low concentrations of unlabeled paf (5 and 10 nM, not 50 nM). Neither lyso-paf nor LPC and enantio paf (not shown) interfered with the [$^3$H]paf binding. Values are calculated as final per $2.5 \times 10^5$ eosinophils and are means±1 s.d. of indicated experiments. Table I shows that low concentration of paf decrease the inhibitory effect of WEB 2086 on human eosinophils.

EXAMPLE 2

Release of Acetylhydrolase from Platelets by High Concentrations of paf

1) Methods

The following reagents were used: Tyrode's buffer was composed of (in mM) NaCl, 137; KCl, 2.68; $NaHCO_3$, 11.9; $MgCl_2$, 1.0; $NaH_2PO_4$, 0.41; dextrose, 0.5; HEPES 5.0. ACD was composed of citric acid (0.8%), trisodic citrate (2.2%) and glucose (2.45%); citric acid (0.15M) (all from Merck-Darmstadt, Germany). Aspirin was used as lysine salt (Aspegic, Egic laboratory, Amilly, France). Fatty acid free bovine serum albumin (BSA) was purchased from Sigma Chemicals Co (St. Louis, Mo.). Human fibrinogen (grade L, pretreated with diisopropylfluorophosphate and partially purified was a gift from B. B. Vargaftig, Institute Pasteur, Paris, France) was obtained from Kabi (Stockholm, Sweden). The kits for lactic dehydrogenase (LDH) was purchased from Boehringer Mannheim (Mannheim, Germany). Thrombin was obtained from Hoffmann-La-Roche (Basel, Switzerland). Zwittergent$^R$ detergent 3.16 was purchased from Calbiochem (Frankfurt, Germany).

Radiolabeled [$^3$H]octadecyl ( 1 -O-[$^3$H]octadecyl-2-acetyl-GPC, 80–120 Ci/mmol) and [$^3$H]lyso-paf (1-O-[$^3$H] octadecyl-GPC, 80–120 Ci/mmol) and the scintillation liquids Biodegradable Counting Scintillant (BCS) and Organic Counting Scintillant (OCS) were purchased from Amersham (Bucks, U.K.). [$^3$H]acetyl paf (1-O-octadecyl-2-[$^3$H]acetyl-GPC, 10 Ci/mmol) was obtained from New England Nuclear (Boston, Mass.). Paf (1-O-octadecyl-2-acetyl-GPC), lyso paf (1-O-octadecyl-GPC) and AAGPC (1-O-hexadecyl-2-palmitoyl-GPC) were purchased from Bachem (Bubendorf, Switzerland).

1.2. Aggregation of platelets.

Washed platelets were prepared and aggregated as described by Korth et al. (Eur. J. Pharmacol. 1988, 152, 101). Briefly, human blood was collected in ACD 1:7 (v/v) and platelet rich plasma (PRP) was obtained after centrifugation at 100×g for 15 min. PRP was centrifuged at 900×g for 10 min. The supernatant (plasma) centrifuged again to discard remaining platelets and was kept on ice for the acetylhydrolase assay. Platelets were washed twice in Tyrode's buffer. After 30 min incubation with 0.1 mM aspirin, platelets were resuspended at the concentration of $2 \times 10^9$ cell per ml and were diluted to a final count of $3 \times 10^8$ cells per 300 µL Tyrode's buffer (pH 7.4) in the presence of 1.3 mM $CaCl_2$ and 0.16 mg/ml fibrinogen. Platelets were aggregated with unlabeled paf (0.1 to 5 nM) or [$^3$H] octadecyl paf (0.65 nM, 15 nCi) for 3 min under stirring at 20° C. or 37° C. in the absence or presence of 0.25% BSA. The extent of platelet aggregation was calculated as percent of maximal light transmission.

1.3. Metabolism of [$^3$H]octadecyl paf in the presence of intact or damaged platelets.

Platelets ($5 \times 10^7$ cells/500 µL) were incubated with [$^3$H] octadecyl paf (0.65 nM, 15 nCi) without stirring at pH 7.4 for 30 min, 1 hr and 2 hr either at 20° C. or 37° C. Incubations were also performed in the presence of BSA. In some experiments platelets were incubated at pH 9.5 for 30 min at 37° C. either in the presence or absence of BSA. Platelet lysis was assessed by the amount of LDH in supernatants.

1.4. Extraction method and liquid chromatography.

After incubation with labeled paf platelet suspensions or corresponding supernatants were extracted as previously described (Korth et al. 1988, Eur. J. Pharmacol. 152, 101). Dichloromethane/methanol (1:2, v/v) was added to platelets suspensions (0.5 ml) for 24 hr at 4° C. and then dichloromethane/water (1:1, v/v) containing 2% acetic acid was added. Organic phases were collected and water phases were washed three times with 1 volume of dichloromethane. The combined organic phases were brought to dryness under an air flow at 40° C. Dry residues were dissolved in small volumes of mobile phases (dichloromethane/methanol/water 60:50:5, v/v/v) and then applied to a Microporasil column 3.9 mm ID×300 mm length (Waters Associates, Milford, Mass.), which was eluted at a flow rate of 1 ml/min as described (Benveniste et al., 1979, CR. Acad. Sci. Paris 289, 1037). Void volume was defined as 3–7 min and 11–13 min as alkylacyl-GPC, 18–21 min as paf and 28–31 min as lyso paf using appropriate authentic standards. Radioactivity in the fractions counted using OCS scintillation liquid and was expressed, after subtraction of background values, as percentage of the sum of radioactivity in all fractions. All water phases were also counted to monitor total radioactivity.

1.5. Acetylhydrolase assay.

Acetylhydrolase activity was measured in lysates from resting or thrombin-aggregated platelets, in supernatants of stimulated platelets and in autologous plasma. Platelets were suspended in Tyrode's buffer (pH 6.4) without BSA at a concentration of $10^9$ platelets per ml, platelet-free plasma (diluted 1:200, v/v in Tyrode's buffer) were added with Zwittergent detergent 3.16 (0.0015% w/v, final concentration) and were sonicated (6 pulses of 10 sec, at 4° C., Bronson Sonic Power Co., Danbury, Conn.). Protein content was determined in cell lysates or plasma using the method as described (Lowry 1951, J. Biol. Chem. 193, 265). Lysates from $5 \times 10^7$ platelets (50 µL containing 80 µg protein), supernatants from thrombin-activated platelets (50 µL, 5 µg protein), or diluted plasma (1/200, 50 µL, 20 µg protein) were added to 440 µL of a buffer (p.H 8.0) containing HEPES 4.2 mM, NaCl 137 mM, KCl 2.6 mM and EDTA 2 mM. After 5 min proincubation at 37° C., the reaction was initiated by addition of 10 µL [$^3$H]acetyl paf (0.01 µCi, 0.5 to 35 µM final concentration). The specificity of acetylhydrolase towards paf was determined by addition of AAGPC (20 µM) to the assay mixture together with [$^3$H]acetyl paf (10 µM). Assay mixtures were incubated for 10 min at 37° C. unless stated otherwise, and stopped by cooling in an ice bath. Two methods were used to separate [$^3$H]acetate from unreacted [$^3$H]acetyl paf with similar results as verified in preliminary studies. The first one as described (Palmantier et al, 1989, Biochem. Biophys. Res. Commun. 162, 475) with modifications, was based on the extraction of [$^3$H]acetyl paf in the organic phase by adding 2 ml methanol/dichloromethane (1:1, v/v) and 0.4 ml acetate (5%) solution containing [14C]acetate (6000 dpm) as an internal standard. Mixtures were centrifuged at 5000×g for 10 min) to facilitate phase separation. The amount of [$^3$H] acetate in the aqueous phase resulting from the acetylhydrolase assay was determined by liquid scintillation counting using BCS as solvent. The second method used to separate [$^3$H]acetate from unreacted [$^3$H]acetyl paf was described (Miwa et al. 1988, J. Clin. Invest. 82, 1983) with some modifications. It was based on addition of an excess of BSA (17.2 mg/600 µL, final concentration) and subsequent precipitation of [$^3$H]acetyl paf bound to added BSA by TCA (7%, v/v, final concentration, 30 min 0° C.). Denaturated proteins were centrifuged at 5000×g for 15 min and the released [$^3$H]acetate was measured by liquid scintillation counting in BCS. Blanks performed using either heat-denaturated (100° C. for 10 min) or acid-treated (p.H. 2.0) enzyme were less than 5% of counts. Blanks were subtracted prior to calculations of enzyme activities. Results are expressed in pmol/min/mg protein after correction for extraction losses estimated using [$^{14}$C]acetate-internal standard. The thermolability of acetylhydrolase in supernatants was checked by heating for 30 min at 65° C. before addition of [$^3$H]acetyl paf.

1.5. Statistical analysis.

Results are expressed as mean±S.D. or S.E as indicated. Statistics were performed using the "Mann Whitney" test (n=3, n=5 or n=6 as indicated).

2. Results 2.1. Lack of paf metabolism during platelet aggregation at low concentrations of paf.

Figure 3A:
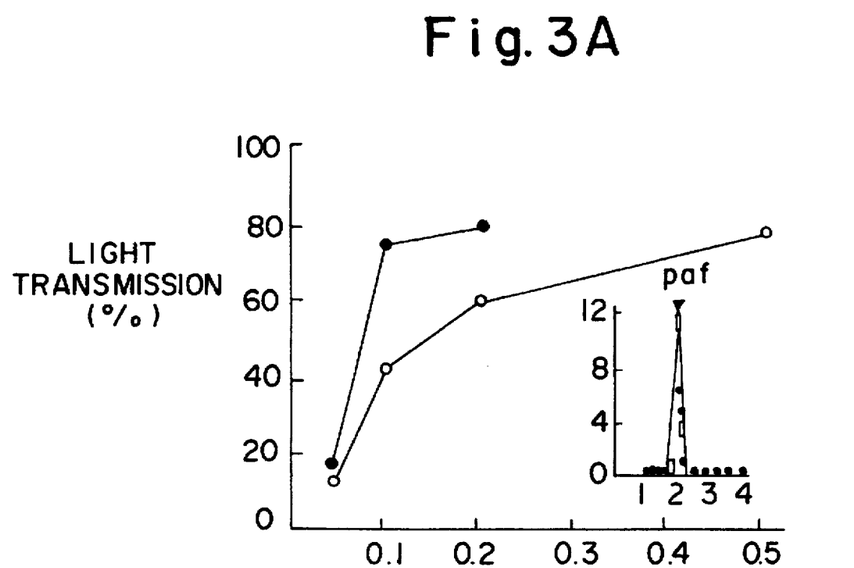
FIG. 3 is a plot of concentration-dependent platelet aggregation with paf and inhibition by BSA.
Figure 3B:
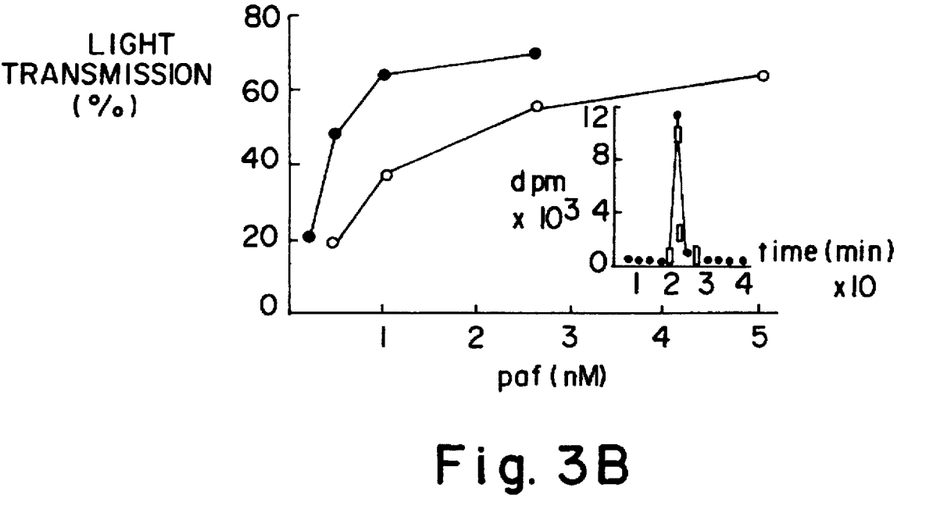

Paf was not metabolized during platelet aggregation in response to low concentrations of paf (0.1 to 5 nM) despite of experimental conditions in the absence or presence of BSA either at 20° C. or at 37° C. (FIG. 3, A and B). The paf concentration inducing 50% of the maximal aggregation ($EC_{50}$) in the absence of BSA was 0.07±0.01 nM and 0.1±0.02 nM at 20° C. and 37° C., respectively (mean±S.E., n=3). Maximal aggregation was reached after 3 min at 0.2±0.02 and 0.5±0.02 nM paf at 20° C. and 37° C., respectively (FIG. 3A). BSA (0.25%) inhibited paf-mediated platelet aggregation; $EC_{50}$ values increased to 0.4±0.1 and 0.9±0.2 nM paf after 3 min aggregation with a maximal aggregation at 2.6±0.5 and 5.0±0.5 nM paf at 20° C. and 37° C., respectively (FIG. 3B).

2.2. Stability of [$^3$H]octadecyl paf in the presence of intact platelets and its catabolism in the presence of damaged platelets.

When intact platelets were incubated with [$^3$H]octadecyl paf (0.65 nM) without stirring either at 20° C. (not shown) or 37° C. and either in the presence or in the absence of 0.25% BSA for 30 min, 1 hr and 2 hr, [$^3$H]octadecyl paf was not degraded (Table 2). Only 4.5% of the label was recovered as [$^3$H]alkylacyl-GPC and 3.5% as [$^3$H]lyso paf at 37° C. in the absence of BSA (pH 7.4). Platelets were essentially undamaged since LDH release was less than 9% vs 4.6±0.4% in supernatants of control cells. However, when platelets were incubated with [$^3$H]octadecyl paf at pH 9.5 in the absence of BSA (30 min, 37° C.) 5.7±3.1% of the label was recovered as [$^3$H]alkylacyl-GPC and 20.5±5.7% as [$^3$H]lyso paf. Under these experimental conditions platelets were damaged; and LDH activity of up to 38% of total was measured in the supernatants.

2.3. Release of acetylhydrolase during platelet aggregation with thrombin or high concentrations of paf.

Platelets released a fraction of their acetylhydrolase content during aggregation in response to thrombin or high concentrations of paf (Table 3). No increase in LDH release was observed after thrombin activation (Table 2) or in response to 100 nM paf (1.5%, n=2). Unstimulated platelets did not release acetylhydrolase (Tables 2). Thrombin (0.5 IU/ml) and paf (500 nM) released only 17.2±3.1% and 10.3±1.5% (mean±S.E., n=3) of the total acetylhydrolase, respectively. These data indicate that the releasable pool of the enzyme is limited. When platelets were incubated for 30 min (37° C.) at pH 9.5, 14.7±4.9% and 37.5±2.5% (mean±S.E., n=3) of acetylhydrolase and LDH were respectively released.

2.4. Kinetic studies of acetylhydrolase.

Figure 4A:
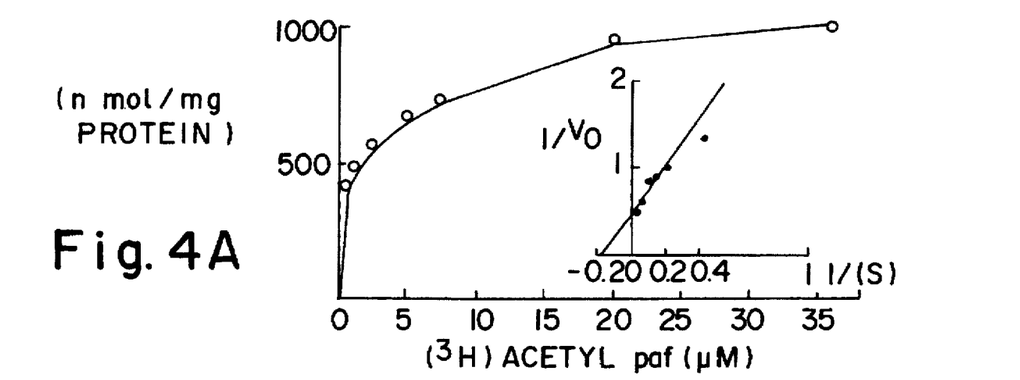
FIG. 4 is a plot of the putative origin of plasma acetylhydrolase from activated platelets shown with acetylhydrolase kinetic constants.
Figure 4B:
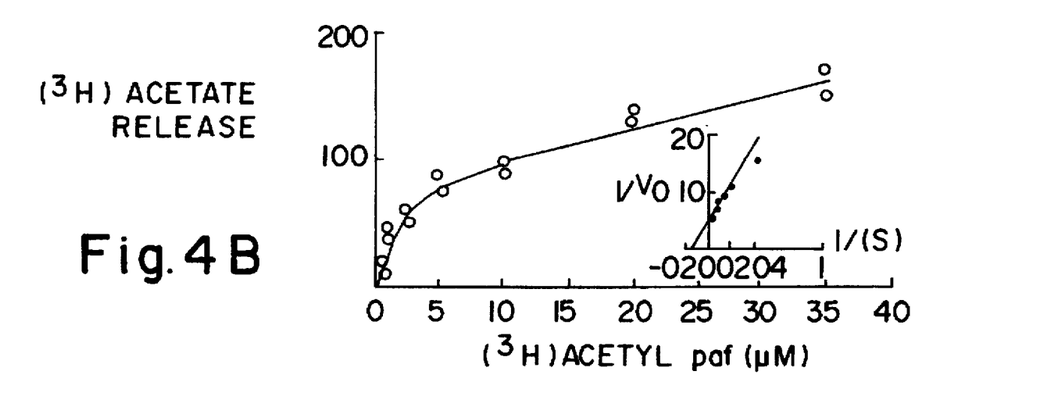
Figure 4C:
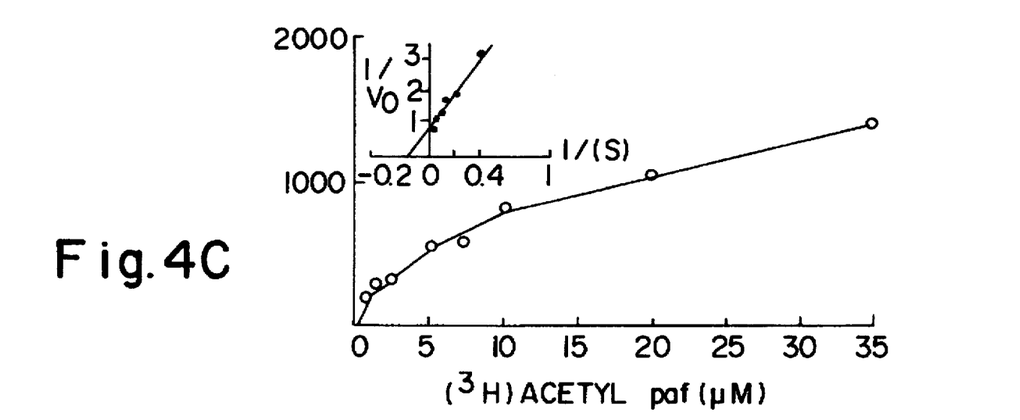

The acetylhydrolase activity was measured in plasma (FIG. 4A), in cell lysates (cells and supernatants) from non-activated and thrombin-activated platelets (FIG. 4, B) and in supernatants from thrombin-activated platelets (FIG. 4, C). The acetylhydrolase activity in all preparations was linear with the time of incubation through at least 10 min and with the protein concentration up to 100 µg/ml (data not shown). Under these conditions [$^3$H]acetate release from [$^3$H]acetyl paf reached nearly a plateau at 20–40 µM (FIG. 4). The acetylhydrolase activity was independent of the presence of $Ca^{2+}$ in the assay, and was not inhibited by excess AAGPC (1-O-hexadecyl-2-palmitoyl-GPC, data not shown), suggesting that the activity that we measured was not the classical phospholipase $A_2$ type.

The affinity of the acetylhydrolase for paf ($K_m$ values) was calculated from the Lineweaver Burk plot (Table 4). The stastical analysis of the data showed a significant difference of the $K_m$ values when measured in the supernatants of thrombin-activated platelets as compared to lyzed platelet and to autologous plasma (n=5, p<0.05). The release of acetylhydrolase from paf and thrombin-activated platelets decreased the $K_m$ value similar to that found in the plasma suggesting that the enzyme microenvironment modify the plasma acetylhydrolase which originates from activated platelets.

The $v_{max}$ calculated for acetylhydrolase from FIG. 4 are shown in Table 4. These values were calculated in relation to the total protein content of the assay (not shown) and not to the pure acetylhydrolase protein. Thus they reflect the relative enrichment in acetylhydrolase of the supernatants obtained from the thrombin-activated platelets in comparison to the cell lysate.

3. Legends and Tables

FIG. 3. Concentration-dependent platelet aggregation with paf and inhibition by BSA.

Platelets ($3\times10^8$/ml) were incubated with defined concentrations of paf in the absence (A) or in the presence of 0.25% BSA (B) at 20° C. (●) or 37° C. (○) under stirring for 3 min. Values are calculated as percent of maximal light transmission. One experiments is representative of three (mean±S.E. is given In the results section). Insets: Lack of paf metabolism under conditions of platelet aggregation. Platelets were incubated with 15 nCi of 0.65 nM [$^3$H]octadecyl paf at 20° C. (●) or 37° C. (○) under stirring for 3 min (100%= 22648±900. dpm, mean±S.E., n=3). Phospholipids were analyzed using liquid chromatography as described in Materials and Methods. FIG. 3 shows an inhibitory effect of BSA and the lack of acetylhydrolase release of intact human platelets.

FIG. 4. The putative origin of plasma acetylhydrolase from activated platelets shown with acetylhydrolase kinetic constants.

The kinetic properties of acetylhydrolase were studied at 37° C. for 10 rain using 5 to 35 μM of paf and 0.1 μCi/500 μL of [$^3$H]acetyl paf. The Lineweaver-Burk plots of the data are given in insets of each figure. A, plasma (20 μg protein/ml); B, lysates (80 μg protein/ml) from resting (●) or thrombin (0.5 IU/ml)-activated platelets (○); C, supernatants from thrombin-activated platelets (5 μg protein/ml). The kinetic data are shown in Table 4 and indicate an origin of the plasma acetylhydrolase from paf- and thrombin-activated platelets.

TABLE 2

Paf Metabolism by Resting, Damaged or Activated Platelets[a]

| Treatment of platelets | LDH (% release) | Lyso paf | Alkylacyl-GPC (%) |
|---|---|---|---|
| (1) BSA | 4.6 ± 0.4(3) | 0.7 ± 0.7 | 1.5 ± 0.8 (3) |
| (2) — | 9.0 (2) | 3.5 ± 0.6 | 4.5 ± 1.8 (4) |
| (3) 30 min, BSA, pH 9.5 | 13.0 (2) | 10 | 0 (1) |
| (4) 30 min, pH 9.5 | | 20.5 ± 5.7 | 5.7 ± 3.1 (4) |
| (5) supernatant of 4 | 37.5 ± 2.5 (3) | 20.1 ± 1.0 | 2.7 ± 1.3 (3) |
| (6) Supernatants of thrombin-activated | 6.5 ± 1.5 (3) | 29.0 | 2.2 (2) |

[a]Treated or untreated platelets (for 1 and 2 pooled results of 30, 60 and 120 min experiments were used) or their supernatants were incubated with [$^3$H]octadecyl paf (15 nCl, 0.65 nM) for 30 min at 37° C. Labeled phospholipids were extracted and analyzed as described in Materials and Methods. Results are in percentage of total counts (22 645 ± 900 dpm) are mean ± S.E. of (n) independent experiments. Table 2 shows the release of acetylhydrolase from activated and damaged platelets

TABLE 3

Time-Course of Acetylhydrolase from Stimulated Platelets[a]

| Stimulation (sec): | Paf (500 nM) | Thrombin (0.5 IU/ml) |
|---|---|---|
| 0 | 1.0 ± 1.0 | 2.2 ± 0.9 |
| 15 | 6.2 ± 3.2 | 8.5 ± 0.7 |
| 30 | 7.6 ± 2.6 | 13.1 ± 3.9 |
| 60 | 9.5 ± 4.0 | 12.8 ± 5.1 |

TABLE 3-continued

Time-Course of Acetylhydrolase from Stimulated Platelets[a]

| Stimulation (sec): | Paf (500 nM) | Thrombin (0.5 IU/ml) |
|---|---|---|
| 120 | 10.0 ± 1.4 | 10.9 ± 3.1 |
| 160 | 12.6 ± 3.8 | 17.9 ± 2.6 |
| 300 | 10.3 ± 1.5 | 17.2 ± 3.1 |

[a]Results are expressed as percentage of the total content of acetylhydrolase and show a time dependent release of acetylhydrolase from paf- and thrombin-activated human platelets. Values are means ± 1 s.d. of three experiments. FIG. 3 shows that paf and thrombin release acetylhydrolase from human platelets.

TABLE 4

Kinetic Constants of Acetylhydrolase[a]

| Source of acetylhydrolase | $K_m$ (μM) | Specific activity $v_{max}$ (nmol/min/mg protein) |
|---|---|---|
| (1) Platelets | 8.33 ± 1.5 | 0.3 |
| (2) Thrombin-activated platelets | 10.6 ± 1.5 | 0.3 |
| (3) Supernatant from (2) | 7.9 ± 1.5* | 1.4 |
| (4) Native plasma | 5.3 ± 0.5*** | 1.4 |

[a]Acetylhydrolase activity was measured in lysates of resting platelets or platelets stimulated with thrombin (0.5 IU/ml, 1 min, 37° C.), in supernatants of thrombin-activated platelets with or without acid-treated (inactivation of acetylhydrolase) plasma and in native plasma. Samples were incubated for 10 min at 37° C. in the presence of 0.1 μCi [$^3$H]acetyl paf and concentrations of cold paf varying from 5 to 35 μM. Results are mean ± S.D. of 5 separate experiments. Values showed significant differences in a "Mann Whitney" test(3 vs 2 and 3 vs 4 *p<0.05; 4 vs 1: ***p<0.003; n.s.; 2 vs 1 and 4 vs 4). The results show a modulation of the acetylhydrolase by its microenvironment and indicate the origin of plasma acetylhydrolase from paf- and thrombin-activated platelets.

EXAMPLE 3

The Paf Antagonist WEB 2086 Inhibits Partly the Increase of cAMP Levels of a Cell Line 1.1. Methods Materials. U 937 cells were a gift from Dr. B. Polla (University of Geneva), RPMI 1640 culture medium, fetal calf serum and L-glutamine were from Serva (Heidelberg., F.R.G.). The delipidated fetal calf serum CPSR 1, isobutyl-1-methylxanthine (IBMX), IoA and essentially fatty-acid-free bovine serum albumin (BSA, fraction V) were from Sigma (St. Louis, Mo., U.S.A.). The RIANEN [$^{125}$I] cAMP Radioimmunoassay (RIA) Kit for cyclic adenosine monophosphate was from Du Pont Company (Billerica, Mass., USA). WEB 2086 was dissolved in destilled water with 0.1M HCL and sonicated. Ascorbinic acid was from Merck (Darmstadt, FRG). Hanks Hepes buffer (HH-buffer) was from Biochem A.G. (F.R.G.). Tyrode's buffer contained 137 mM NaCl, 2.68 mM KCl, 11.9 mM $NaHCO_3$, 1.0 mM $MgCl_2$, 0.41 mM $NaH_2PO_4$, 0.5 mM dextrose, 5 mM Hepes (pH 7.4). HBSS buffer was from Biochem. A.G. (Germany).

1.2. Cell culture:

U 937 cells were grown in stationary suspension culture in RPMI 1640 containing 10% FCS and 2 mM L-glutamine at 37° C. in a humidified atmosphere of 5% $CO_2$ and 95% air. The cells were diluted with fresh medium (1/10, v/v) twice a week. After three days in culture U 937 cells were centrifuged (1000×G for 10 min) and incubated for 24 hrs in RPMI 1640 medium containing 10% CPSR 1 (delipidated FCS) and 2 mM L-glutamine. Subsequently they were incubated in the delipidated FCS medium containing cholesterol (10–60 µg/ml), as compared with cholesterol vehicle (ethanol, 0.5% v/v, final concentration) for (2, 4 or 24 hrs).

Radioimmunoassay of cAMP: Cyclic AMP levels of supernatants from cholesterol-treated and control cells, were measured by the Rianen [$^{125}$I]cAMP-RIA Kit. Briefly, cholesterol (60 µg/ml, 24 hrs) or cholesterol vehicle (ethanol) were added after 24 hrs cell incubation delipidated FCS medium before cells were subsequently washed three times in Tyrode's buffer. They were resuspended ($5 \times 10^6$, final concentration ) in HH-buffer, pH 7.4 with ascorbinic acid (10 mM) and the cAMP-phosphodiesterase Inhibitor IBMX. (1 mM). The cell suspension (100 µl) was added to 400 µl of the cAMP buffer for 30 min at 20° C. The reaction was started with increasing concentrations of paf with and without WEB 2086 (1 µM) and stopped in an ice bath after 5 min incubation at 37° C. Proteins were denaturated (100° C., 5 min) and centrifuged (5 min with 1500×G, 20° C.). Values are from one experiment (representative of three) were expressed as pmol cAMP per $10^6$ U 937 cells. Total proteins were measured in parallel as described (Lowry et al., 1951, J. Biol. Chem. 193, 265).

Figure 5:
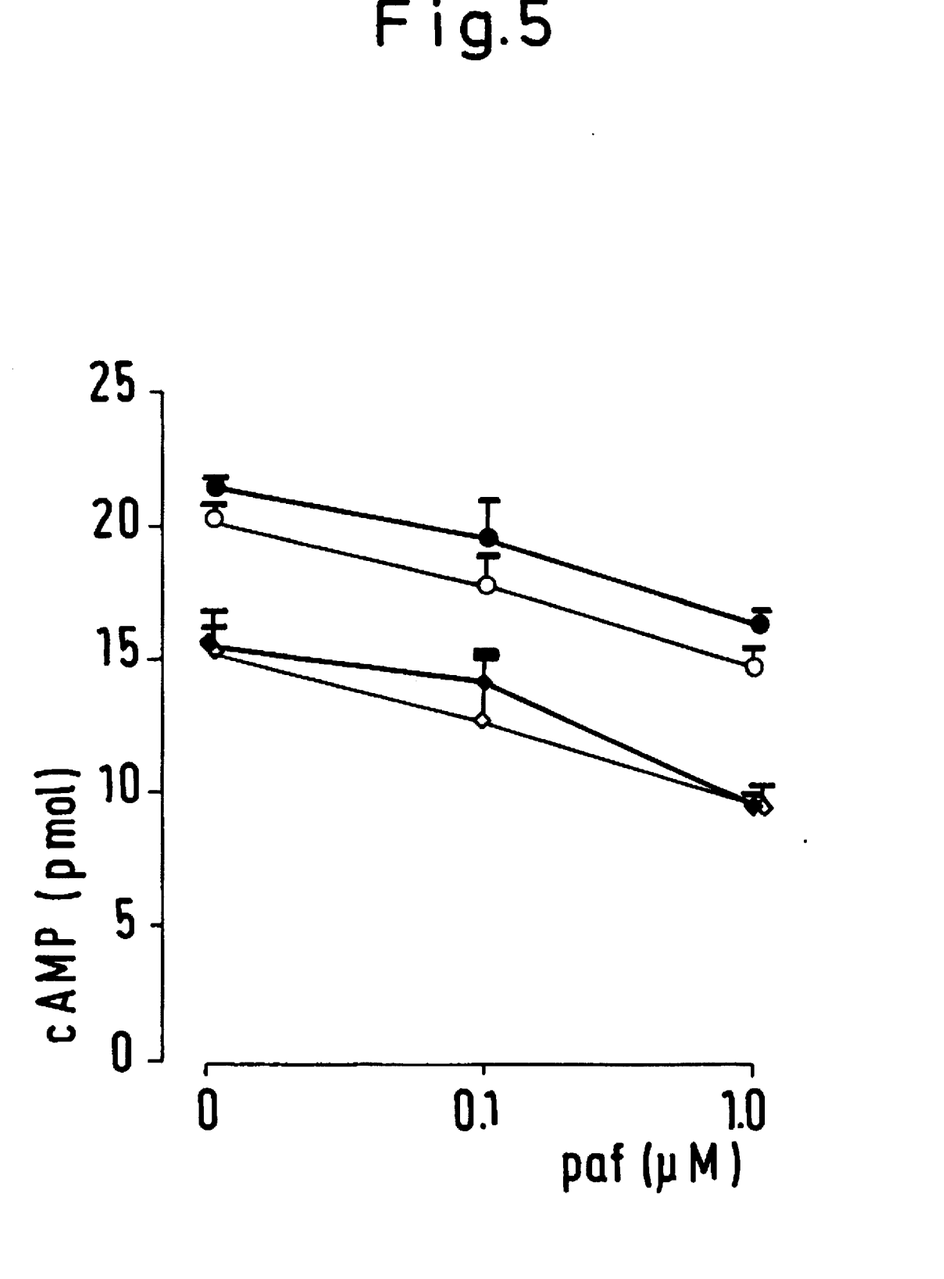
FIG. 5 is a plot of paf dose response curve for cAMP synthesis.

2. Results 2.2.) Cholesterol treatment and cAMP levels of U 937 cells:

Cholesterol expressed specific paf binding sites as described (R. Korth patent application 91108763.3). FIG. 5 shows an increase of cAMP levels in monocyte/macrophage like cells which expressed paf receptors after 24 hrs incubation with cholesterol. This increase of cAMP was only partly inhibited by the paf receptor antagonist WEB 2086.

3. Legend

FIG. 5. Paf dose response curve for cAMP synthesis.

The cAMP levels were measured in the presence (○◊) and absence (●♦) of WEB 2086 (1 µM) of monocyte/macrophage like U 937 cells after addition of cholesterol (60 µg/ml, 24 hrs) (●○) a compared with control cells (♦ ◊). Values are expressed as pmol cAMP per $1 \times 10^6$ U 937 cells (means±1 s.d., n=3). FIG. 5 shows that the increase of cAMP in response to long lasting Cell activation which express paf receptors is only partly prevented by the paf receptor antagonist WEB 2086.

I claim:

1. A method of treating or preventing oedema comprising topically administering to a patient in need of such treatment an effective amount of a topically applicable composition comprising tetrahydro-4,7,8,10-methyl(chloro-2-phenyl)6 (dimethoxy-3,4-phenyl)thiomethylthiocarbonyl-9-pyrido (4',3'-4,5)thieno(3,2-f)triazolo-1,2,4(4,3-a)diazepine-1,4) and N-3 polyunsaturated fatty acids.

* * * * *